(12) United States Patent
Haugaard et al.

(10) Patent No.: US 8,911,373 B2
(45) Date of Patent: Dec. 16, 2014

(54) VECTOR FLOW ULTRASOUND IMAGING

(75) Inventors: Per Haugaard, Skovlunde (DK); Gert Seerup, Hilleroed (DK)

(73) Assignee: B-K Medical Aps, Herlev (DK)

( * ) Notice: Subject to any disclaimer, the term of this patent is extended or adjusted under 35 U.S.C. 154(b) by 30 days.

(21) Appl. No.: 13/613,099

(22) Filed: Sep. 13, 2012

(65) Prior Publication Data

US 2013/0261456 A1 Oct. 3, 2013

Related U.S. Application Data

(60) Provisional application No. 61/619,519, filed on Apr. 3, 2012.

(51) Int. Cl.
*A61B 8/00* (2006.01)

(52) U.S. Cl.
USPC ............ 600/441; 600/437; 600/443; 600/447

(58) Field of Classification Search
None
See application file for complete search history.

(56) References Cited

U.S. PATENT DOCUMENTS

| 5,105,816 | A | 4/1992 | Shimura et al. | |
|---|---|---|---|---|
| 5,855,557 | A | 1/1999 | Lazenby | |
| 5,910,119 | A | 6/1999 | Lin | |
| 6,148,224 | A | 11/2000 | Jensen | |
| 2005/0043622 | A1* | 2/2005 | Jensen | 600/449 |
| 2008/0009737 | A1* | 1/2008 | Takimoto et al. | 600/454 |
| 2008/0269611 | A1* | 10/2008 | Pedrizzetti et al. | 600/454 |

OTHER PUBLICATIONS

Udesen, et al., Examples of In Vivo Blood Vector Velocity Estimation, Ultrasound in Med & Biol., 2007, pp. 541-548, vol. 33, No. 4.
EFSUMB Newsletter, Demonstration of a Vector Velocity Technique, Ultraschall in Med, 2011, pp. 213-216, vol. 32.
Pedersen, et al., Comparison of Real-Time In Vivo Spectral and Vector Velocity Estimation, Ultrasound in Med & Biol., 2012, pp. 145-151, vol. 38, No. 1.

* cited by examiner

*Primary Examiner* — Mark Remaly
(74) *Attorney, Agent, or Firm* — Anthony M. Del Zoppo, III; Driggs, Hogg, Daugherty & Del Zoppo Co., LPA

(57) ABSTRACT

An ultrasound imaging console includes receive circuitry that receives a set of echoes produced in response to an ultrasound signal traversing blood flowing in a portion of a vessel in a field of view, a beamformer that beamforms the echoes, a velocity processor that determines flow direction and magnitude of the flowing blood based on the beamformed echoes, and a rendering engine that displays the determined flow direction and magnitude.

26 Claims, 5 Drawing Sheets

VECTOR FLOW ULTRASOUND IMAGING

CROSS REFERENCE TO RELATED APPLICATIONS

This application claims the benefit of U.S. provisional application Ser. No. 61/619,519 filed Apr. 3, 2012, which is incorporated herein by reference.

TECHNICAL FIELD

The following generally relates to ultrasound imaging and more particularly to vector flow ultrasound imaging.

BACKGROUND

Ultrasound imaging provides information about the interior of a subject. For example, ultrasound imaging can be used to generate an image of a blood vessel and estimate blood flow velocity inside the blood vessel.

With conventional blood flow velocity estimation, a pulse-echo field oscillates in the axial direction along the axis of the ultrasound beam. This is illustrated in FIG. 1 in which a transducer array 100 produces an ultrasound beam 102 that propagates in the axial direction along the z-axis (or depth) 104. Blood scatterers passing through the field of interest produce a signal with a frequency component proportional to the axial velocity, and the axial velocity component (VZ) 106 can be estimated.

The transverse oscillation (TO) blood velocity estimation approach has been used to estimate both VZ 106 and the transverse velocity component (VX) 108, along the transverse axis 110, of the velocity vector 112. With the transverse oscillation approach, a transverse oscillation is introduced in the ultrasound field, and this oscillation generates signals that depend on the transverse oscillation. The basic idea is to create a double-oscillating pulse-echo field using a one dimensional (1D) transducer array.

Color flow mapping (CFM) is one approach to visually show velocity. An example of this is shown in FIG. 2, in which first flow 202 through a first vessel 204 and second flow 206 through a second vessel 208 towards the transducer is displayed using a first color (red shades), and third flow 210 through the first vessel 204 and fourth flow 212 through the second vessel 208 away from the transducer is displayed using a second different color (blue shades). Intensity is proportional to the velocity of the flow.

Unfortunately, with color flow mapping, the two colors only show relative flow with respect to the ultrasound transducer. Furthermore, with color flow mapping, blood flow perpendicular to the ultrasound beam cannot be seen. Moreover, with color flow mapping, the colors do not indicate the direction and magnitude of the blood flow. In view of at least the above, there is an unresolved need for other approaches for visualizing blood flow.

SUMMARY

Aspects of the application address the above matters, and others.

In one aspect, an ultrasound imaging console includes receive circuitry that receives a set of echoes produced in response to an ultrasound signal traversing blood flowing in a portion of a vessel in a field of view, a beamformer that beamforms the echoes, a velocity processor that determines flow direction and magnitude of the flowing blood based on the beamformed echoes, and a rendering engine that displays the determined flow direction and magnitude.

In another aspect, a method includes receiving a set of echoes produced in response to an ultrasound signal traversing blood flowing in a portion of a vessel in a field of view, beamforming the echoes, estimating flow direction and magnitude of blood the flowing blood based on the beamformed echoes, and displaying the determined flow direction and magnitude.

A computer readable storage medium is encoded with computer readable instructions, which, when executed by a processer, cause the processor to: receive a set of echoes produced in response to an ultrasound signal traversing blood flowing in a portion of a vessel in a field of view, beamform the echoes, estimate flow direction and magnitude of blood the flowing blood based on the beamformed echoes, generate an image based on the beamformed echoes, and displaying indicia representing flow direction and magnitude superimposed over the image, wherein flow direction is displayed using at least one of color or hue and magnitude is displayed using intensity.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
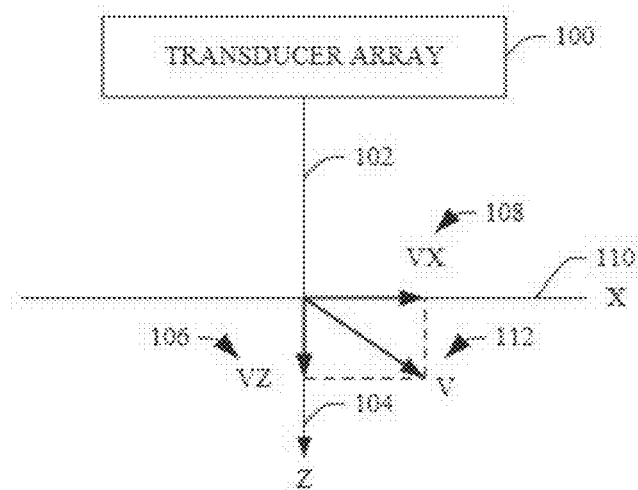
FIG. 1 illustrates a prior art approach to estimating blood flow velocity along the axial and transverse direction of a vessel.
Figure 2:
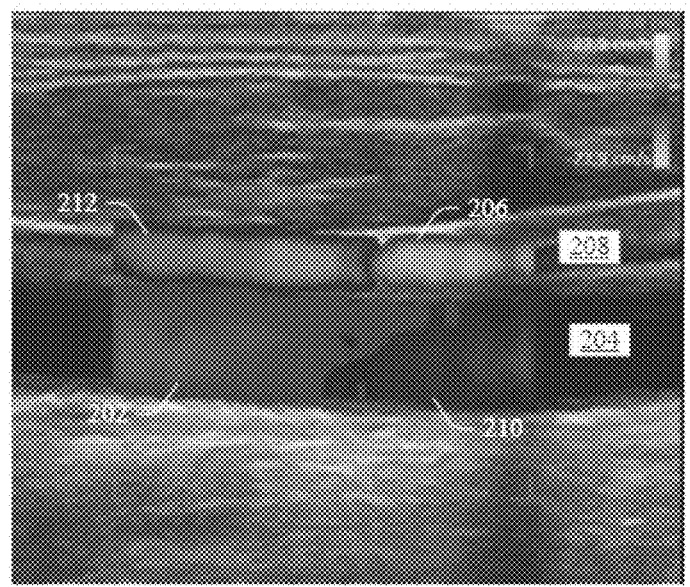
FIG. 2 illustrates a prior art color flow mapping approach for visualizing flow direction relative to the position on the ultrasound transducer.
Figure 3:
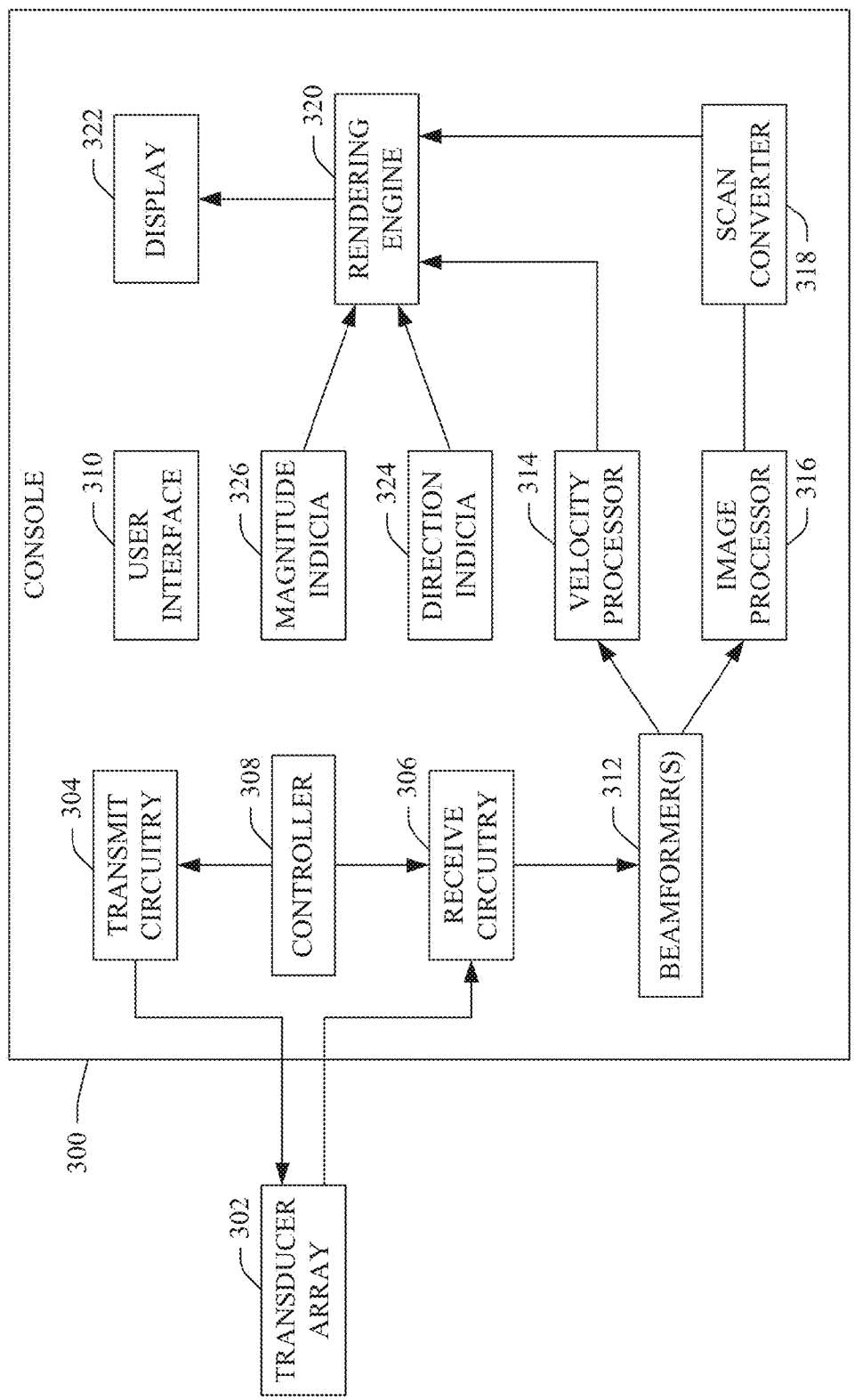
FIG. 3 illustrates an example ultrasound scanner configured to visually present blood flow absolute direction and magnitude.

Initially referring to FIG. 3, an example ultrasound imaging console 300 is illustrated.

A transducer array 302 includes a one dimensional (1D) array of transducer elements, which are configured to transmit ultrasound signals and receive echo signals. Examples of suitable 1D arrays include 128, 192, and/or other dimension arrays, including square and/or rectangular arrays. The array can be linear, curved, and/or otherwise shaped. The array can be fully populated or sparse and/or a combination hereof.

Transmit circuitry 304 generates a set of pulses that are conveyed to the transducer array 302. The set of pulses actuates a corresponding set of the transducer elements of the transducer array 302, causing the elements to transmit ultrasound signals into an examination or scan field of view. In the illustrated embodiment, transmit circuitry 304 generates a set of pulses which produce a transmit signal suitable at least for velocity imaging.

Receive circuitry 306 receives echoes generated in response to the transmitted ultrasound signals from the transducer 302. The echoes, generally, are a result of the interaction between the emitted ultrasound signals and the structure (e.g., flowing blood cells, organ cells, etc.) in the scan field of view.

A controller 308 controls one or more of the transmit circuitry 304 or receive circuitry 306. Such control can be based on available modes of operation (e.g., velocity flow, A-mode, B-mode, etc.) of the system 300. In addition, such control can be based on one or more signals indicative of input from a user.

A user interface (UI) 310 produces the one or more signals indicative of the input from a user. The UI 310 may include one or more input devices (e.g., a button, a knob, a slider, a touch pad, etc.) and/or one or more output devices (e.g., a display screen, lights, a speaker, etc.).

One or more beamformers 312 process the echoes, for example, by applying time delays, weighting on the channels, summing, and/or otherwise beamforming received echoes.

A velocity processor 314 processes the beamformed data. In one instance, this includes processing the beamformed data using a transverse oscillation (TO) approach and determining from the processed data one or more velocity components such as a depth (VZ) velocity component and a transverse (VX) velocity component, including direction and magnitude of flow. The TO approach is described in greater detail in U.S. Pat. No. 6,148,224 to Jenson, titled "Apparatus and Method for Determining Movement and Velocities of Moving Objects, filed on Dec. 30, 1998, and assigned to B-K Medical A/S, which is incorporated herein by reference in its entirety.

An image processor 316 also receives the beamformed data. For B-mode, the image processor 316 processes the data and generates a sequence of focused, coherent echo samples along focused scanlines of a scanplane. The image processor 316 may also be configured to process the scanlines to lower speckle and/or improve specular reflector delineation via spatial compounding and/or perform other processing such as FIR filtering, IIR filtering, etc.

A scan converter 318 scan converts the output of the image processor 316 to generate data for display, for example, by converting the data to the coordinate system of the display. The scan converter 318 can be configured to employ analog and/or digital scan converting techniques.

A rendering engine 320 visually presents one or more images with blood flow information via a graphical user interface (GUI) in a display monitor 322. With respect to flow imaging, the image may include a 2D angular independent flow image showing both flow direction and magnitude, where direction is shown in absolute direction, as opposed to conventional Doppler imaging, where flow is shown towards and away from the ultrasound probe.

In one instance, hue is used for direction and intensity is used for magnitude based on direction indicia 324 and magnitude indicia 326. Additionally or alternatively, graphics, such as vectors, flowlines, particles, animation, and/or other indicia, from the magnitude indicia 326 is used for direction. It is to be appreciated that acquiring angular independent flow information simplifies user manipulation of probe as sonographers do not have to search for the best scan angle. This also allows for a reduction in examination time.

Less training is required to interpret the images since the flow information in both direction and magnitude is visualized. Furthermore, the displayed image can show complex flow such as turbulence or flow vortex in a vessel, such as the carotid artery, the jugular vein, and/or other blood vessel. Moreover, the peak measured transverse velocity component can be two times larger than the peak measured axial component for the same depth. This opens doors to areas where there is a desire to measure fast blood flow parallel to the transducer surface, such as the flow in the fistulas of hemodialysis patients.

It is to be appreciated that the components 312, 314 and/or 316 can be implemented via one or more processors executing one or more computer readable instructions encoded or embedded on computer readable storage medium such as physical memory. Additionally or alternatively, the one or more processors can execute at least one instruction(s) carried by a carrier wave, a signal, or other non-computer readable storage medium such as a transitory medium.

Figure 4:
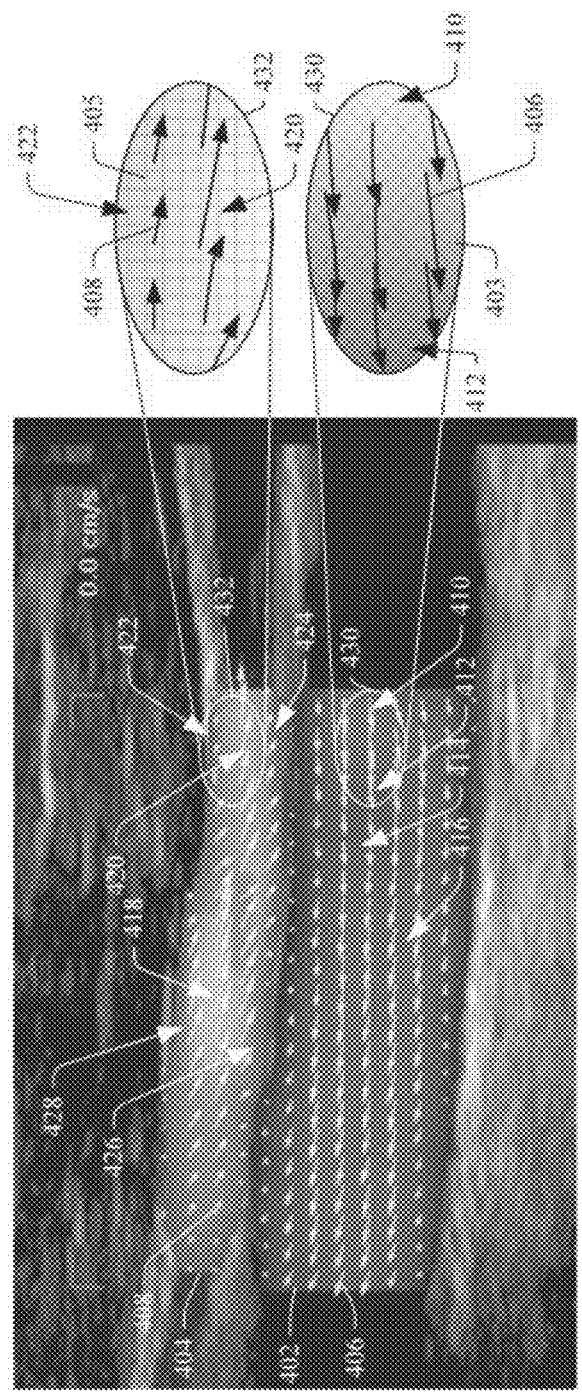
FIG. 4 illustrates an example visualization of blood flow absolute direction and magnitude along the axial direction.
Figure 5:
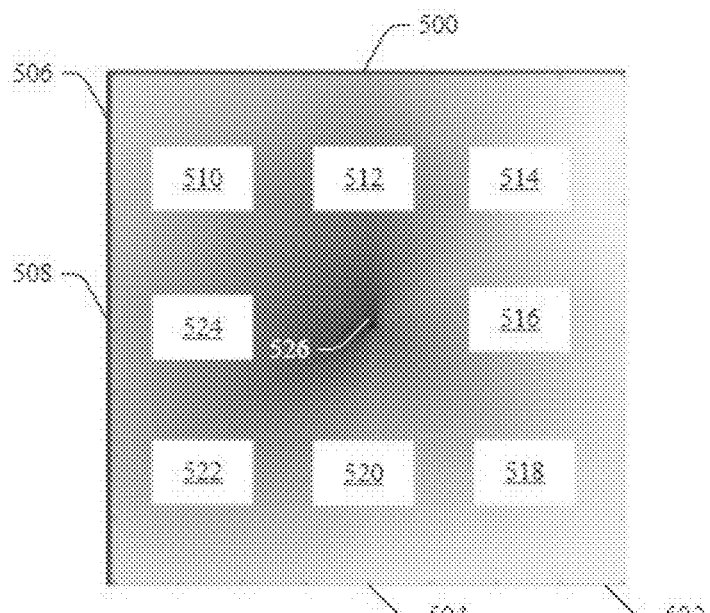
FIG. 5 illustrates an example 2D blood flow direction-magnitude map.

FIGS. 4 and 5 illustrate an example in which flow direction is shown using graphical indicia (i.e., vectors) and flow direction and magnitude is shown using a two-dimensional color-intensity mapping.

In FIG. 4, vessel portions 402 and 404 along long axes of the vessels are shown.

Vectors 406 in the vessel 402 show flow direction going right to left, generally horizontally or slightly downward at the far right to acutely upward at the far left. Vectors 408 in the vessel 404 show flow going left to right, acutely downward most of the length of the portion 404.

The portion 402 is highlighted using darker colors 403, which is used to show flow direction from left to right. The portion 404 is highlighted using lighter colors 405, which is used to show flow direction from right to left. Intensity (or brightness) is used to show velocity magnitude, with a higher intensity representing a larger magnitude.

With respect to the portion 402, a region about 410 is higher intensity relative to regions about 412 and 414, and a region 416 has an intensity between the intensity at 410 and 412. With respect to the portion 404, regions about 418 and 420 have higher intensity relative to regions about 422, 424, 426 and 428, which have slightly different intensity.

The vector flow indicia 406 and 408, the darker colors 403 and the lighter 405 colors (represented via different patterns), and the intensities 410 and 412 and the intensities 420 and 422 are further shown in magnified views 430 and 432.

FIG. 5 shows an example velocity direction-magnitude map 500. An x-axis 502 represent a first color scheme representing transverse velocity direction, with zero transverse velocity at 504, and a y-axis 506 represent a second color scheme representing axial velocity direction, with zero axial velocity at 508.

Regions 510, 512, 514, 516, 518, 520, 522 to 524 show several example colors of the map 500. The intensity increases from a center region 526 to the periphery of the map 500.

Figure 6:
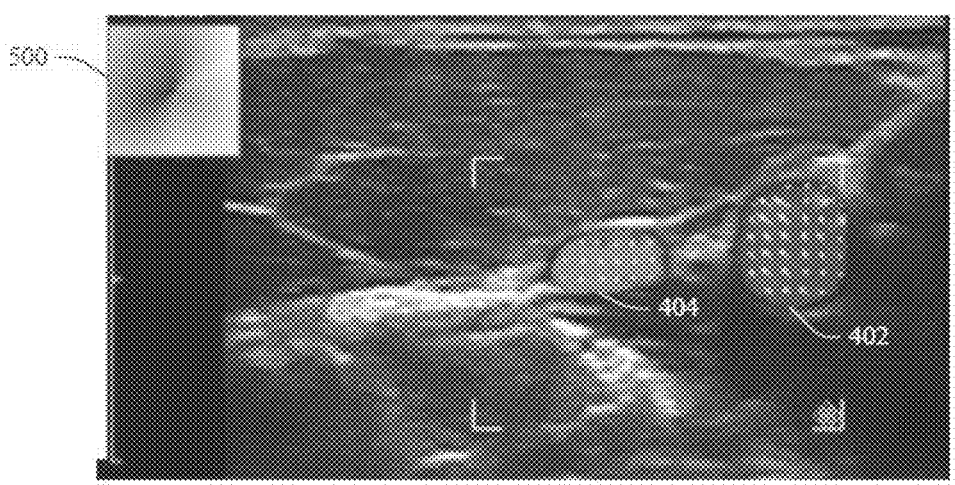
FIG. 6 illustrates example visualization of blood flow absolute direction and magnitude.

FIG. 6 shows the vessel portions 402 and 404 of FIG. 4 in the transverse plane. Likewise, vectors and colors are used to show flow direction and intensity is used to show magnitude. In this embodiment, the color map 500 is concurrently shown.

In FIGS. 4 and 6, quantitative information can be variously obtained. In one instance, hovering a mouse pointer over and/or clicking on a region of the portion 402 and 404 invokes the rendering engine 320 to display a numerical value representing the flow.

In another instance, a curve showing velocity as a function of time is visually presented, which shows how velocity evolves in real-time.

In yet another instance, a velocity profile curve showing velocity as a function of points taken along a line and as a function of time is displayed. Such a curve may useful for vessel surgery and/or other applications.

Figure 7:
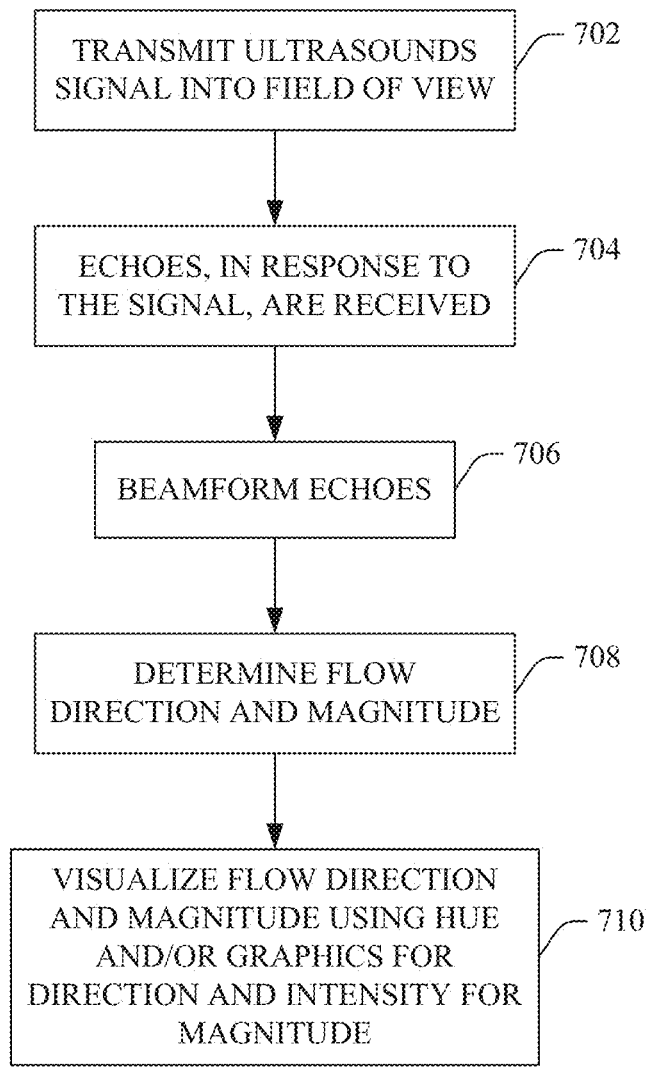
FIG. 7 illustrates a method.

FIG. 7 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 702, an ultrasound signal is transmitted into a field of view.

At 704, echoes, in response to the ultrasound signal, are received by a transducer array.

At 706, the echoes are beamformed.

At 708, flow direction and magnitude are determined.

At 710, the flow direction and magnitude visually presented, for example, with hue and/or graphics showing direction and intensity showing magnitude, superimposed over a B-mode or other image.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging console, comprising:
   receive circuitry that receives a set of echoes produced in response to an ultrasound signal traversing blood flowing in a portion of a vessel in a field of view;
   a beamformer that beamforms the echoes, producing beamformed echoes;
   an image processor that generates an image based on the beamformed echoes;
   a velocity processor that determines flow direction and magnitude of the flowing blood based on the beamformed echoes; and
   a rendering engine that displays the image with graphical indicia representing the determined flow direction and magnitude superimposed thereover, wherein the graphical indicia includes different hues to indicate different flow directions and different intensities to indicate different flow magnitudes, and displays, concurrently with the image and the graphical indicia, a graphical 2D direction-magnitude map that maps the hues of the graphical indicia to directions and the intensities of the graphical indicia to magnitudes.

2. The console of claim 1, further comprising:
   transmit circuitry that generates a control signal that controls transmission of the ultrasound signal that traverses the field of view.

3. The console of claim 1, wherein the flow direction and magnitude are determined using the transverse oscillation approach.

4. The console of claim 1, further comprising:
   direction indicia, wherein the rendering engine further displays the determined flow direction based on the direction indicia.

5. The console of claim 4, wherein the direction indicia includes one or more of graphical vectors, flowlines, animation, or particles.

6. The console of claim 4, wherein the direction indicia corresponds to absolute direction.

7. The console of claim 1, wherein the overlay concurrently includes multiple different hues indicating multiple different flow directions and concurrently includes multiple different intensities indicating multiple different flow magnitudes.

8. The console of claim 7, wherein the flow direction indicia and magnitude indicia provide quantitative information.

9. The console of claim 8, wherein the rendering engine displays a numerical value representing quantitative information corresponding to a region of interest.

10. The console of claim 8, wherein the rendering engine displays a curve showing velocity as a function of time.

11. The console of claim 7, wherein the graphical 2D direction-magnitude map includes a first axis with a first color scheme representing a transverse velocity direction and a second axis second with a second different color scheme representing an axial velocity direction.

12. The console of claim 11, wherein a first central point of the first axis represents zero transverse velocity and a second central point of the second axis represents zero axial velocity.

13. The console of claim 12, wherein a central point of the graphical 2D direction-magnitude map represents zero transverse velocity and zero axial velocity.

14. The console of claim 13, wherein intensity increases from the central point to a periphery of the graphical 2D direction-magnitude map.

15. An apparatus, comprising:
    a memory that stores computer readable instructions;
    a display; and
    a computer processor that executes the computer readable instructions, which causes the computer processor to: process received ultrasound echo signals indicative of flowing structure, generate an image based thereon, determine flow direction information and flow magnitude information based thereon, generate an image overlay with different hues representing different flow directions of the flowing structure and with different intensities representing different flow magnitudes of the flowing structure, and visually present, via the display, the image with the image overlay superimposed thereover.

16. The apparatus of claim 15, wherein the hues and intensities provide quantitative flow information.

17. The apparatus of claim 15, the computer processor further visually presents a plot of velocity as a function of time.

18. The apparatus of claim 15, the computer processor further visually presents a profile showing velocity as a function of points taken along a line as a function of time.

19. The apparatus of claim 15, the computer processor further visually presents, via the display, a graphical legend, which includes hues and intensities overlaid over each other, concurrently with the image and the image overlay.

20. The apparatus of claim 19, wherein the graphical legend includes a first axis with a first color scheme representing a transverse velocity direction and a second axis second with a second different color scheme representing an axial velocity direction.

21. The apparatus of claim 20, wherein a first central point of the first axis represents zero transverse velocity and a second central point of the second axis represents zero axial velocity.

22. The apparatus of claim 21, wherein a central point of the graphical legend represents zero transverse velocity and zero axial velocity.

23. The apparatus of claim 22, wherein intensity increases from the central point to a periphery of the graphical legend.

24. The apparatus of claim 15, wherein the apparatus is part of an ultrasound imaging console.

25. The apparatus of claim 15, the ultrasound imaging console, including:
- transmit circuitry that generates a control signal that control an operation of a transducer array to transmit an ultrasound signal into a field of view; and
- receive circuitry that receives the ultrasound echo signals, which are produced in response to the ultrasound signal interacting with the flowing structure in the field of view.

26. The apparatus of claim 25, the ultrasound imaging console, including:
- the transducer array, which includes an array of transducer elements.

* * * * *